United States Patent [19]
Van Baren et al.

[11] Patent Number: 6,165,725
[45] Date of Patent: Dec. 26, 2000

[54] METHOD FOR DETERMINING REGRESSION OR PROGRESSION OF MULTIPLE MYELOMA

[75] Inventors: Nicolas Van Baren; Francis Brasseur; Thierry Boon-Falleur, all of Brussels, Belgium

[73] Assignee: Ludwig Institute for Cancer Research, New York, N.Y.

[21] Appl. No.: 09/351,351

[22] Filed: Jul. 12, 1999

Related U.S. Application Data

[62] Division of application No. 09/018,422, Feb. 4, 1998, Pat. No. 5,985,571.

[51] Int. Cl.⁷ .............................. C12Q 1/68; C12P 19/34; C07H 21/04; C07Q 1/70
[52] U.S. Cl. ................................. 435/6; 435/5; 435/91.2; 435/91.1; 536/22.1; 536/243
[58] Field of Search .................................. 435/6, 91.2, 5; 536/22.1, 24.3

[56] References Cited

U.S. PATENT DOCUMENTS

| | | | |
|---|---|---|---|
| 5,512,444 | 4/1996 | Patard et al. ............................. | 435/91.2 |
| 5,612,201 | 3/1997 | De Plaen et al. ........................ | 435/91.2 |
| 5,763,165 | 6/1998 | Boon-Falleur et al. ..................... | 435/6 |

*Primary Examiner*—W. Gary Jones
*Assistant Examiner*—Joyce Tung
*Attorney, Agent, or Firm*—Fulbright & Jaworski, LLP

[57] ABSTRACT

Methods for diagnosing multiple myeloma are disclosed. These methods are based upon the observation that tumor rejection antigen precursors are expressed in multiple myeloma. By assaying bone marrow samples, one can diagnose multiple myeloma, and also monitor the disease's progress. Therapeutic approaches of multiple myeloma are also disclosed.

10 Claims, 1 Drawing Sheet

FIG. 1

Multiple Myeloma (MM) staging system (Durie and Salmon)

STAGE I - All of the following criteria

1 - Hemoglobin value > 10 g/100 ml
2 - Serum calcium value normal ≤ 12 mg/100 ml
3 - On roentgenogram, normal bone structure (scale O) or solitary bone plasmacytoma only
4 - Low M-component production rates a) IgG value < 5 g/100 ml
   b) IgA value < 3 g/100 ml
   c) urine light chain M-component on electrophoresis < 4g/24 h.

STAGE II - Fitting neither stage I nor Stage III

STAGE III - One or more of the following criteria

1 - Hemoglobin value < 8.5 g/100 ml
2 - Serum calcium value > 12 mg/100 ml
3 - Advanced lytic bone lesions scale 3
4 - High M-component production rates a) IgG value > 7 g/100 ml
   b) IgA value > 5 g/100 ml
   c) Urine light chain M-component on electrophoresis > 12 g/24 h.

Subclassification :

A = relatively normal renal function (serum creatinine value < 2.0 mg/100 ml)
B = abnormal renal function (serum creatinine value ≥ 2.0 mg/100 ml)

SEQUENCE LISTING

<160> NUMBER OF SEQ ID NOS: 12

<210> SEQ ID NO 1
<211> LENGTH: 22
<212> TYPE: DNA
<213> ORGANISM: Artificial sequence
<220> FEATURE:
<221> NAME/KEY: oligonucleotide primer

<400> SEQUENCE: 1
cggccgaagg      aacctgaccc      ag                              22

<210> SEQ ID NO 2
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 2
gctggaaccc      tcactgggtt      gcc                             23

<210> SEQ ID NO 3
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 3
aagtaggacc      cgaggcactg                                      20

-continued

```
<210> SEQ ID NO 4
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 4
gaagaggaag   aagcggtctg                                                  20

<210> SEQ ID NO 5
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 5
tggaggacca   gaggccccc                                                   19

<210> SEQ ID NO 6
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 6
ggacgattat   caggaggcct   gg                                             22

<210> SEQ ID NO 7
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 7
gagcagacag   gccaaccg                                                    18

<210> SEQ ID NO 8
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 8
aaggactctg   cgtcaggc                                                    18

<210> SEQ ID NO 9
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 9
tggaggacca   gaggccccc                                                   19

<210> SEQ ID NO 10
<211> LENGTH: 24
<212> TYPE: DNA
<213> ORGANISM: Artificial sequence
<220> FEATURE:
```

-continued

```
<223> OTHER INFORMATION: Oligonucleotide primer

<400> SEQUENCE: 10
caggatgatt    atcaggaagc    ctgt                                        24

<210> SEQ ID NO 11
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 11
cgttggaggt    cagagaacag                                                20

<210> SEQ ID NO 12
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 12
gccctccact    gatctttagc    aa                                          22
```

METHOD FOR DETERMINING REGRESSION OR PROGRESSION OF MULTIPLE MYELOMA

RELATED APPLICATION

This application is divisional of U.S. patent application Ser. No. 09/018,422, filed Feb. 4, 1998, now U.S. Pat. No. 5,985,571, and is incorporated by reference.

FIELD OF THE INVENTION

This invention relates to cancer diagnosis. More particularly, it relates to members of the "tumor rejection antigen precursor" family referred to as MAGE. These, especially MAGE-1, 2, 3, 4, 6 and 12 have been identified as "markers" for multiple myeloma.

BACKGROUND AND PRIOR ART

The study of the recognition or lack of recognition of cancer cells by a host organism has proceeded in many different directions. Understanding of the field presumes some understanding of both basic immunology and oncology. Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum- variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum⁻ antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application and incorporated by reference, teaches a family of human tumor rejection antigen precursor coding genes, referred to as the MAGE family, including MAGE-1, 2, 3, 4, 6 and 12. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. A U.S. application corresponding in part to this PCT application has issued as U.S. Pat. No. 5,342,774, and is incorporated by reference herein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that, in some cases a nonapeptide is presented on the surface of tumor cells, and that the presentation of the nonapeptide requires that the presenting molecule be HLA-A1. Complexes of the MAGE-1 tumor rejection antigen (the "TRA" or nonapeptide") leads to lysis of the cell presenting it by cytolytic T cells ("CTLs"). Additional research has correlated other nonapeptides derived from MAGE and genes to HLA-A1 and other MHC class I molecules.

Research presented in, e.g., U.S. Pat. No. 5,405,940, incorporated by reference, showed that, when comparing homologous regions of various MAGE genes to the region of the MAGE-1 gene coding for the relevant nonapeptide, there is a great deal of homology.

The nucleic acid sequences which code for the nonapeptides were also described therein. These nucleic acid sequences were described as also being useful as diagnostic probes for tumor presence.

The patent also shows how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The co-transfectant could be used to determine whether the particular MAGE based TRA is presented by the particular HLA molecule.

Many of the references referred to supra present data on the expression pattern of various MAGE genes in different types of cell lines and tumor tissues. What is evident from these data is that there is no "unifying principle" which allows one to predict which MAGE gene will be expressed by a particular tumor type. Thus, while on one level one can say that MAGE genes are "markers" for tumors, on the level of specific tumor types, the correlation of marker and tumor type is not predictable, and must be determined empirically.

This invention relates to the identification of expression of MAGE tumor rejection antigen precursors, especially MAGE-1, 2, 3, 4, 6 and 12 in myeloma, multiple myeloma in particular. Methods for determining presence of these conditions, and reagents useful in the assays, are the subject matter of the invention.

BRIEF DESCRIPTION OF THE FIGURES

FIG. 1 presents the standard staging system of Durie and Salmon, Cancer 36(3): 842–854 (1975) incorporated by reference. Also see DeVita et al., Cancer, Principles In Practice of Oncology, 4th Edition, 1995.

DETAILED DESCRIPTION OF PREFERRED EMBODIMENTS

Primers

The following is a list of the primers used in the assays which follow infra:

5'-CGGCCGAAGGAACCTGACCCAG-3' (sense) (SEQ ID NO: 1) and

5'-GCTGGAACCCTCACTGGGTTGCC-3' (anti-sense) (SEQ ID NO: 2) for MAGE-1

5'-AAGTAGGACCCGAGGCACTG-3' (sense) (SEQ ID NO: 3) and

5'-GAAGAGGAAGAAGCGGTCTG-3' (anti-sense) (SEQ ID NO: 4) for MAGE-2

5'-TGGAGGACCAGAGGCCCCC-3 (sense) (SEQ ID NO: 5) and

5'-GGACGATTATCAGGAGGCCTGC-3' (antisense) (SEQ ID NO: 6) for MAGE-3

5'-GAGCAGACAGGCCAACCG-3' (sense) (SEQ ID NO: 7) and

5'-AAGGACTCTGCGTCAGGC-3' (anti-sense) (SEQ ID NO: 8) for MAGE-4

5'-TGGAGGACCAGAGGCCCCC-3 ' (sense) (SEQ ID NO: 9), and

5'-CAGGATGATTATCAGGAAGCCTGT-3' (antisense) (SEQ ID NO: 10) for MAGE 6,

5'-CGTTGGAGGTCAGAGAACAG-3' (sense) (SEQ ID NO: 11), and

5'-GCCCTCCACTGATCTTTAGCAA-3' (antisense) (SEQ ID NO: 12) for MAGE 12.

SEQ ID NO: 11 is new. SEQ ID NOS: 1–10 and 12 may be found in, e.g., DePlaen et al., Immunogenetics 40: 360–369 (1994) incorporated by reference.

EXAMPLE 1

PCR assays were carried out using the above referenced primers, generally following DePlaen et al., Immunogenetics 40: 360–369 (1994), and Patard et al., Int J. Cancer 64: 60–64 (1995), both of which are incorporated by reference. Specifically, each PCR reaction contained 5 ul of cDNA, obtained as described infra, supplemented with 5 ul of 10×PCR buffer, 1 ul each of 10 mM dNTP, 0.5 ul each of 80 uM solutions of primers, 3 ul of 25 mM $MgCl_2$ 1.25 units of Taq polymerase, and water to bring the reaction volume to 50 ul. Mixtures were then heated to 94° C. for five minutes, followed by thermocycling for 30 cycles. For MAGE-1, one cycle was one minute at 94° C. followed by three minutes at 72° C. For MAGE-2, a cycle was one minute at 94° C., followed by two minutes at 67° C., and two minutes at 72° C. For MAGE-3, a cycle was one minute at 94° C. and four minutes at 72° C. For MAGE-4, a cycle was one minute at 94°, two minutes at 68° C., and two minutes at 72° C.

For MAGE-6, one cycle was one minute at 94° C., followed by two minutes at 70° C. and two minutes at 72° C. For MAGE-12, 32 cycles were carried out, each cycle being one minute at 94° C., two minutes at 62° C., and three minutes at 72° C.

The primers listed supra were used in PCRs, using conditions listed supra, on multiple myeloma bone marrow samples. For each sample, mononucleated cells from anticoagulated bone marrow or blood were purified, washed three times with culture medium and then phosphate buffered saline. Following centrifugation, a cell pellet was obtained, dried, and stored at −80° C.

Total RNA was extracted from the pellets, using standard methods, and then cDNA was synthesized, following Weynants, et al., Int. J. Cancer 56: 826–829 (1994), incorporated by reference. Following synthesis of cDNA, the above referenced protocols were carried out. The results of the assays are given in Table 1, which follows:

The column making reference to "stage" refers to standard diagnostic parameters for multiple myeloma, following Durie and Salmon, supra, incorporated by reference. These parameters are set forth in FIG. 1.

The foregoing data demonstrate the features of the invention. One aspect of the invention is the ability to determine presence of myeloma, multiple myeloma in particular, and especially late stage multiple myeloma, by assaying a sample for expression of a MAGE tumor rejection antigen precursor. Most preferably, the sample is a bone marrow sample. While PCR has been exemplified, the artisan of ordinary skill will recognize that any hybridization assay, including nucleic acid amplification assays, may be used. It is especially preferred to use one or more hybridization probes which are specific to one of MAGE 1, 2, 3, 4, 6 or 12. These are preferably 17–50 nucleotides in length, more preferably 17–25 nucleotides in length. One can assay for one, or more than one, of the MAGE species listed supra. Other MAGE genes may also be expressed by these myeloma cells. "MAGE" encoding nucleic acid molecules, or "MAGE gene", as used herein, refers to any of the genes described in the literature as a MAGE family member. Exemplary but by no means exclusive, are the genes and sequences set forth in U.S. Pat. No. 5,342,774, incorporated by reference, as well as sequences which hybridize to the sequences listed therein under the stringent conditions provided. Also see PCT/US92/04354, also incorporated by reference, and cited supra, as well as DePlaen and Patard, incorporated by reference and cited supra.

| | | | | | MAGE RT-PCR results | | | | | | | | |
|---|---|---|---|---|---|---|---|---|---|---|---|---|---|
| N° | code N° | sex | diagn/stage | idiotype | 1 | 2 | 3 | 4 | 6 | 12 | β-actin | sample | % plasmo |
| 1 | LB-1736 | M | MGUS | IgG Kappa | − | − | − | − | − | − | normal | BM | 6 |
| 2 | LB-1584 | M | MM/IA | IgG Lambda | − | − | − | − | − | − | normal | BM | 25 |
| 3 | LB-1602 | F | MM/IA | IgG Kappa | − | − | − | − | − | − | normal | BM | 43 |
| 4 | LB-1604 | M | MM/IA | IgA Kappa | − | − | − | − | − | − | normal | BM | 10–15 |
| 5 | LB-1584 | M | MM/IA | IgG Lambda | − | − | − | − | − | − | normal | BM | 31 |
| 6 | LB-1738 | F | MM/IB | IgG Kappa | − | − | − | − | − | − | normal | BM | 11 |
| 7 | LB-1599 | F | MM/IIA | IgA Kappa | − | − | − | − | − | − | normal | BM | 21 |
| 8 | LB-1731 | F | MM/IIA | IgG Kappa | − | − | − | − | − | − | normal | BM | |
| 9 | LB-1536 | M | MM/IIIA | Lambda | +++ | +++ | + | − | ++ | ++ | normal | BM | 45 |
| 10 | LB-1601 | M | MM/IIIA | IgG Kappa | − | + | + | ± | + | − | very weak | BM | 89 |
| 11 | LB-1654 | F | MM/IIIA (PCL) | IgG Kappa | − | − | − | − | − | − | weak | PBL | 14 |
| 12 | LB-1669 | F | MM/IIIA | IgG Kappa | ± | − | − | − | +++ | − | normal | BM | 85 |
| 13 | LB-1673 | M | MM/IIIA | Kappa | − | − | − | − | − | − | normal | BM | 14 |
| 14 | LB-1724 | M | MM/IIIA | IgA Kappa | − | − | ± | − | − | − | normal | BM | 5 |
| 15 | LB-1723 | F | MM/IIIA | IgG Kappa | + | ± | + | − | + | + | normal | BM | 17 |
| 16 | LB-1740 | M | MM/IIIA | IgA Kappa | − | − | − | ± | + | − | normal | BM | 32 |
| 17 | LB-1784 | F | MM/IIIA | IgA Lambda | + | − | ± | − | − | − | normal | BM | >90 |
| 18 | LB-1787 | M | MM/IIIA | IgG Lambda | +++ | ± | ++ | − | − | ± | normal | BM | 81 |
| 19 | LB-1744 | F | MM/IIIB | IgA Kappa | ± | ± | − | − | ++ | − | normal | BM | >70 |
| 20 | LB-1752 | F | MM/IIIB | IgA Kappa | ± | − | − | − | − | − | normal | BM | 100 |
| 21 | LB-1785 | F | MM/IIIB | Kappa | +++ | +++ | +++ | + | +++ | + | normal | PBL | 47 |
| 22 | LB-1149 | F | MM/IIIB (PCL) | IgA Kappa | ± | − | − | − | − | − | normal | PBL | 43 |
| 23 | LB-1596 | M | MM/IIIB | IgG Kappa | − | − | − | − | − | − | normal | BM | 24 |
| 24 | LB-1626 | F | MM/IIIB | Lambda | −/± | − | ± | − | −/± | −/± | normal | BM | 68 |

MGUS = monoclonal gammopathy of unknown significance
MM = multiple myeloma
PCL = plasma cell leukemia
BM = bone marrow
PBL = peripheral blood leukocytes Peripheral blood was used for a few samples, because circulating myeloma cells were identified therein. The results for β-actin were used as a control. It may be useful to note that "% plasmo" as used in Table 1 refers to the proportion of malignant plasmocytes following visual analysis of a bone marrow aspirate, via microscopy. In multiple myeloma, the standard range is 15%–100%.

Another aspect of the invention is a method for monitoring the course of a therapeutic regime. As will be noted, the MAGE sequences are expressed, for the most part, in late stage, i.e., stage III, myeloma. In the course of treatment (e.g., chemotherapy, immunotherapy, bone marrow transplant, etc.), as myeloma regresses, one can monitor this by noting loss or decrease in MAGE expression relative to a level determined at a prior point in time. Similarly, development of the disease, relapse, response to bone marrow transplant, etc., can be monitored by observing increases. This can be accomplished via, e.g., polymerase chain reaction ("PCR") RT-PCR being preferred or other hybridization assays.

Additional diagnostic methods include assays of precursor T cells or cytolytic T cells specific for complexes of MHC molecules and MAGE derived peptides. These can be determined via, e.g., chromium release, tumor necrosis factor ("TNF"), ELISPOT, soluble complexes of MHC/MAGE peptides labelled, e.g., fluorescently or with some other signalling label, or with multimeric peptide complexes, and so forth. These types of assay are useful before, during, and after the therapeutic treatments described, supra.

The recognition that MAGE molecules are implicated in multiple myeloma has therapeutic ramifications as well. One may, for example, treat the subject in an appropriate way such that cytolytic T lymphocytes recognize and destroy those cells which present tumor rejection antigens on their surface.

For example, it is known that various MAGE-derived peptides function as T cell epitopes, in that they are presented by MHC class I molecules, with the resulting complex being recognized and lysed by cytolytic T cells. Exemplary, but by no means limiting, are the peptides disclosed in U.S. Pat. No. 5,405,940, the disclosure of which is incorporated by reference. The ability to provoke proliferation of autologous T cells in vitro, via contact of blood samples to complexes of peptide and MHC molecules is well known. The resulting autologous cytolytic T cells can be reinfused to the subject from whom the blood samples was taken, after which the cytolytic T cells enter the bone marrow. It is known that plasma cells express MHC molecules. See, e.g., Yi et al., Blood 90(5): 1960–1967 (1997), incorporated by reference. Hence, the reinfused CTLs would target the plasma cells which present the MAGE derived peptides on their surface, presenting complexes identical to these used to generate the CTLs in vitro.

Similarly, one can envision treatment methodologies which employ dendritic cells, pulsed with the peptide epitopes alluded to supra, as well as cells which have been treated so as to present relevant complexes on their surfaces. Such cells may be transformed or transfected with a MAGE gene or genes, a MAGE "minigene" or "minigenes", which encodes only relevant MHC binding peptides such as tumor rejection antigens, and/or a relevant MHC-molecule encoding sequence, such as HLA-A1, A2, Cw6, and so forth. If appropriate, such cells may be irradiated prior to administration.

Other features of the invention will be clear to the skilled artisan and need not be set forth herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for determining regression or progression of multiple myeloma comprising assaying a bone marrow sample of a patient diagnosed with multiple myeloma previously for expression of a nucleic acid molecule which encodes a MAGE protein, and comparing level of expression determined to a prior level of expression of said MAGE protein, in said patient variation therebetween indicating progression or regression of said multiple myeloma.

2. The method of claim 1, wherein said nucleic acid molecule encodes MAGE-1, MAGE-2, MAGE-4, MAGE-6, or MAGE- 12 protein.

3. The method of claim 1, comprising determining expression of said nucleic acid molecule via a nucleic acid hybridization assay.

4. The method of claim 1, comprising determining expression of said nucleic acid molecule via polymerase chain reaction.

5. The method of claim 3, wherein said nucleic acid hybridization assay comprises contacting said bone marrow sample with at least one oligonucleotide molecule consisting of from 17–50 nucleotides which hybridizes specifically to said nucleic acid molecule which encodes a MAGE protein.

6. The method of claim 5, wherein said oligonucleotide molecule consists of 17–25 nucleotides.

7. The method of claim 5, wherein said, at least one, oligonucleotide molecule consists of the nucleotide sequence set forth in SEQ ID NO: 1, 2, 3, 4, 5, 6, 7, 8, 9, 10, 11 or 12.

8. The method of claim 4, wherein said polymerase chain reaction comprises contacting said bone marrow sample with a pair of oligonucleotide primers selected from the group consisting of: (i) SEQ ID NOS: 1 and 2, (ii) SEQ ID NOS: 3 and 4, (iii) SEQ ID NOS: 5 and 6, (iv) SEQ ID NOS: 7 and 8, (v) SEQ ID NOS: 9 and 10, and (vi) SEQ ID NOS: 11 and 12.

9. The method of claim 1, wherein said bone marrow sample is taken from a patient who has undergone or is undergoing chemotherapy immunotherapy, or bone marrow transplant therapy.

10. The method of claim 1, wherein said patient is suffering from stage III myeloma.

* * * * *